(12) United States Patent
Schwarz et al.

(10) Patent No.: US 7,138,394 B2
(45) Date of Patent: Nov. 21, 2006

(54) VEHICLE FOR TOPICAL DELIVERY OF ANTI-INFLAMMATORY COMPOUNDS

(75) Inventors: Joseph Schwarz, Richmond Hill (CA); Michael Weisspapir, Richmond Hill (CA)

(73) Assignee: Alpharx Inc., Markham (CA)

( * ) Notice: Subject to any disclaimer, the term of this patent is extended or adjusted under 35 U.S.C. 154(b) by 301 days.

(21) Appl. No.: 10/255,951

(22) Filed: Sep. 27, 2002

(65) Prior Publication Data

US 2004/0063794 A1    Apr. 1, 2004

(51) Int. Cl.
*A61K 31/54* (2006.01)
*A61K 31/165* (2006.01)
*A01N 37/18* (2006.01)

(52) U.S. Cl. .................. 514/226.5; 514/359; 514/621; 514/622

(58) Field of Classification Search ............... 514/743, 514/226.5, 359, 621, 622
See application file for complete search history.

(56) References Cited

U.S. PATENT DOCUMENTS

| 4,316,887 | A | * | 2/1982 | Kamishita et al. ......... 514/692 |
| 4,731,200 | A | | 3/1988 | Lang et al. .................... 512/5 |
| 4,933,184 | A | | 6/1990 | Tsuk .......................... 424/449 |
| 5,013,726 | A | | 5/1991 | Ivy et al. .................... 514/159 |
| 5,124,320 | A | | 6/1992 | Ivy et al. .................... 514/159 |
| 5,144,081 | A | | 9/1992 | Heywang et al. ........... 568/326 |
| 5,175,152 | A | | 12/1992 | Singh ......................... 514/162 |
| 5,322,689 | A | | 6/1994 | Hughes et al. .............. 424/401 |
| 5,376,688 | A | | 12/1994 | Morton et al. .............. 514/786 |
| 5,853,768 | A | | 12/1998 | Altadonna .................. 424/667 |
| 5,961,997 | A | * | 10/1999 | Swinehart ................... 424/401 |
| 6,113,921 | A | | 9/2000 | Friedman et al. ........... 424/400 |
| 6,447,817 | B1 | * | 9/2002 | Niyiro et al. ............... 424/742 |

FOREIGN PATENT DOCUMENTS

JP          54046818     *   4/1979

OTHER PUBLICATIONS

Handbook of Pharmaceutical Excipients, Third Edition, ed. A.H. Kibbe, Pharmaceutical Press, London, UK, 2000, pp. 334-335.
Benita S., Levy M. Submicron Emulsions as Colloidal Drug Carriers for Intravenous Administration: Comprehensive Physicochemical Characterization. J. Pharm. Sci Nov. 1993 82(11), pp. 1069-1079.
Kaplun-Frischoof Y, Touitou E. Testerone Skin Permeation Enhancement by Menthol through Formation of Eutectic with Drug and Interaction with Skin Lipids. J. Pharm. Sci. Dec. 1997 86(12), pp. 1394-1399.
Ho, H.; Chen, LC; Lin, H.M.; Sheu, M.T. Penetration Enhancement by Menthol Combined with a Solublization Effect in a Mixed Solvent System. J. Controlled Release Feb. 12, 1998; 51(2-3); pp. 301-311.

* cited by examiner

*Primary Examiner*—Alton Pryor
(74) *Attorney, Agent, or Firm*—McCarthy Tetrault LLP

(57) ABSTRACT

A vehicle for topical delivery which contains a liquid eutectic mixture of hydrophobic compounds.

21 Claims, 2 Drawing Sheets

VEHICLE FOR TOPICAL DELIVERY OF ANTI-INFLAMMATORY COMPOUNDS

FIELD OF THE INVENTION

The present invention relates to the preparation of semi-solid formulations for topical delivery of pharmaceutically active ingredients, designed for pain control and inflammation treatment.

BACKGROUND OF THE INVENTION

Topical pharmaceutical preparations of different types have been used for treatment of rheumatic and arthritic pain for decades. Semisolid compositions comprise plant derivatives, such as capsaicin (red hot pepper stinging substance) or turpentine (pine tar component) ointments, homeopathic extract and liniments (Opodeldoc Rus), mustard plasters, menthol rubs, essential oil balms and many others were used for a long time, mainly as local irritants. Such irritation improves local blood flow, accelerates injured tissue recovery, and switches attention from chronic pain from inflammation.

By including non-steroid anti-inflammatory drugs (NSAIDs) into ointment or cream application onto the desired allows for effective control of muscle and joint pain intensity. Moreover, when NSAIDs are applied topically, local drug concentration in muscle and joint tissues is significantly higher than in non-treated sites. Additionally, there is no intensive metabolism in liver (so called "first-pass effect") because such drugs do not pass through the liver before action.

The required amount of NSAIDs is lower than an oral dose to achieve similar anti-inflammative and analgesic effects. The most common side effect of NSAIDs is serious irritation of stomach and gastro-intestinal mucosa. This is substantially diminished with local topical applications.

Topical NSAID formulations are very popular in Europe, Asia and Far East regions. Examples of compositions include Voltaren Emulgel® (Voltarol™ in UK), a 1.16% Diclofenac diethylammonium emulsion cream with isopropyl alcohol, Feldene® Gel (0.5% Piroxicam water-ethyl alcohol gel), Ibuprofen and Ketoprofen gels of different strengths (5–10%), and 1–10% Indomethacin in alcohol. DMSO-containing creams and many other formulations are widespread in many countries as OTC remedies for muscle pain, sport minor injuries, rheumatic and back pain treatment, etc.

Generally, topical NSAID preparations do not have attributable side-effects such as gastric irritation and internal bleeding. Advantageously, the compounds provide relatively fast action onset and moderate efficacy in treatment of local muscle and joint pain. The main problems of these products is low drug loading due to low solubility in the cream components. High loading can be reached by use of concentrated alcohols, i.e. ethyl alcohol, isopropyl alcohol with polyethylene glycol and propylene glycol suitable as solvents for NSAIDs. Drug loading is high and can easily reach 5–10% or greater, e.g., 5% Ibuprofen gel with isopropyl alcohol, 1% Indomethacin gel based on ethyl alcohol or even 10% Indomethacin ointment with dimethylsulfoxide.

These solvents are widely used for gel preparation, but widespread use is often limited due to the proclivity for skin irritation. A further limitation is realized in fast termination of action for gel preparations since the drug precipitates from solution subsequent to water absorption from the body tissue. Further, solvents in high concentration often irritate the skin due to drying and delipidisation and may initiate contact dermatitis and allergy. Drug, insoluble in water media and body fluids, precipitates in the upper skin layers and does not penetrate inside, seriously limiting anti-inflammatory action. Similar behavior was observed for polyethylene glycol (mixture of PEG-4000 and PEG-400) hydrophilic topical base.

Traditional hydrophobic vehicles such as fixed oils, mineral oil, petrolatum, lanolin and wax based ointments, along with emulsion creams (either O/W or W/O type) are less irritating to human skin, but these present another complication—solubility. Drug loading in such vehicles is limited by the solubility of the drug in the lipid phase. For example, the solubility of Indomethacin in olive or corn oil is below 0.2%, whereas Ketoprofen is about 1.5% and Piroxicam below 0.05%. According to Benita et al. "Submicron Emulsions as Colloidal Drug Carriers for Intravenous Administration: Comprehensive Physicochemical Characterization", J. Pharm Sci., 1993, Nov. 82 (11), pp. 1069–79, even for low drug loading, stability of the dispersed system is questionable. A 0.1% Indomethacin submicron emulsion lost stability after 1 month storage.

Use of more polar hydrophobic compounds may help to improve solubility of NSAIDs. Tocopherol acetate, triethyl citrate, glycerin monolaurate, glycerin monooleate (Myverol™ 18–9) dissolve between 1.5 and 2 times more Indomethacin or Diclofenac (in acidic form). Nevertheless, this loading is insufficient to obtain an effective NSAID emulsion. Transdermal adhesive systems such as skin patches and plasters with Indomethacin or Diclofenac present low efficacy by the same reasoning.

A further method to increase drug solubility in the oil phase is to use highly polar compounds, miscible with named phase. Solvents such as Ethoxyethylene glycol (Transcutol™), dimethylisosorbide (DMIS), Isopropylideneglycerin (Solketal™), ethoxylated furanyl alcohol (Glucofurol™) visibly boost drug implementing in the separate hydrophobic phase. However, upon mixing with water, most of the solvent is extracted into the water and the dissolved drug precipitates immediately and almost entirely from the oil phase.

Recently developed submicron emulsions (SME) employed as a base for NSAIDs, provides very effective delivery and exert pronounced improvement for drug action in Friedman et al. (U.S. Pat. No. 6,113,921). However, low solubility of NSAIDs in a lipid phase of such emulsions leads to shortened periods of efficacy and drug precipitation from the oil phase during storage. High loading, desirable for optimal activity of topical NSAID preparation for SME is achievable only for highly lipophilic compounds, such as Naproxen, Ketoprofen or Ibuprofen with significantly lower anti-inflammatory activity.

Eutectic mixture use in topical applications is rather limited. An example is EMLA cream, developed by AstraZeneca. The liquid, formed by mixing two crystalline bases of local anesthetics, Lidocain and Prilocain due to eutectic formation serves as an oil phase in the cream for topical application. The cream, containing 5% of such oil phase, provides excellent stability and anesthetic action.

In view of the limitation in the anti-inflammatory drug art, there exists a need for an improved composition which overcomes the shortcomings presently encountered.

SUMMARY OF THE INVENTION

It has been found that a eutectic mixture of camphor, menthol, thymol and similar compounds is a powerful solvent for non-steroidal anti-inflammatory drugs and other substances. The solubility of Indomethacin, Diclofenac, or Ketoprofen in the mixture increased between 3 and 20 fold. As a particular advantage, the eutectic mixture was found to be safe, non-toxic and present synergistic behavior in anti-inflammatory action of NSAIDs due to anti-inflammatory properties of camphor and skin penetration enhancing properties of menthol.

The eutectic mixture can be combined with pharmaceutically acceptable oils and lipids and included into topical formulations. The compositions were found to allow much higher drug loading than existing ointment bases and creams, showed no skin irritation and provided enhanced delivery properties for incorporated drugs.

Prior to enhancing on a discussion of the preparation, some general properties of the menthol and camphor will be established.

The menthol used was (1R, 2S, 5R)-5-methyl-2-(1-methyethyl)-cyclohexanol with a molecular weight of 156.27 and melting point of 42° C. Menthol generally has a peppermint odor. It is well known as a skin irritant and penetration enhancer in Tsuk (U.S. Pat. No. 4,933,184). It is widely used in many topical formulations for relief of arthritic and rheumatic pain. Natural L-menthol exerts a cooling or refreshing sensation due to direct interaction with cold sensitive receptors in the skin. This was established in the Handbook of Pharmaceutical Excipients, Third Edition, ed. A. H. Kibbe, Pharmaceutical Press, London, U.K., 2000, pp. 334–335. Menthol has been used as mild local anesthetic and as volatile aromatic component for breath relief in obstruction and cold treatment in Hughes et al. (U.S. Pat. No. 5,322,689).

Similar properties are known for camphor 1,7,7-trimethylbicyclo[2,2,1]heptanone-2, having a molecular weight of 152.24. Camphor has a high melting point (180° C.) and is a very volatile substance with strong pine-like odor that sublimes even at room temperature and pressure. Initially, camphor found use as a stimulant, but now camphor is mainly used as a component in topical preparations. It is often used in nasal decongestants and aromatic compositions.

Either menthol D-isomer, L-isomer, racemic or a mixture of menthol isomorers or camphor D-isomer, L-isomer, racemic or a mixture of camphor isomers separately or in combination are widely used in topical formulations, mainly due to their irritant action, receptor interaction and specific traditional odor, frequently associated with time-honored remedies. Ben Gay™ ointment, Tiger™ balm, Menthol Chest Rub and similar compositions are well known and popular.

Certain external analgesic products containing between 10% to 60% methyl salicylate, more than 3% to 11% camphor and 1.25% to 16% menthol, either singly or in combination, cause irritation or mild inflammation of the skin for the purpose of relieving pain in muscles, joints, or viscera distal to the site of application by stimulating depressing cutaneous sensory receptors in Ivy et al. (U.S. Pat. No. 5,013,726).

Topical preparations for joint relief include that provided for in Lang et al. (U.S. Pat. No. 4,731,200) for an aqueous-alcohol composition containing benzylidene-camphor derivatives, Ivy et al. (U.S. Pat. No. 5,013,726) for a lotion containing methyl salicylate, camphor and menthol, Ivy et al. (U.S. Pat. No. 5,124,320) for an analgesic lotion containing menthol and camphor, Heywang et al. (U.S. Pat. No. 5,144,081) for a pharmaceutical composition containing camphor and Singh (U.S. Pat. No. 5,175,152) for a composition with methyl salicylate, menthol and camphor.

These substances have been advertised for use in relieving joint pain, such as the elbow, knee, thumb area, ankle, neck, wrist, hand and finger, shoulder, etc.

To improve solubility of non-steroidal anti-inflammatory drugs, a complex mixture of surfactants, polyglycol(s) and glycerides has been used in combination with polymers and sodium or potassium hydroxide solutions as established in Morton et al. (U.S. Pat. No. 5,376,688).

In Kaplun-Fischoff et al. "Testosterone Skin Permeation Enhancement by Menthol Through Formation of Eutectic with Drug and Interaction with Skin Lipids", J. Pharm Sci. 1997, December, 86 (12) pp.1394–9, the researchers observed that menthol forms a eutectic mixture with crystalline testosterone. The formed mixture is not liquid, but the composition demonstrated a significant improvement in transdermal penetration of testosterone. According Kaplun-Frischoff et al., menthol affects skin permeation by a dual mechanism: by forming a eutectic with the penetrating compound, thereby increasing its solubility in skin ceramides and by altering the barrier properties of the stratum corneum.

A careful investigation of existing compositions containing menthol and camphor in different ratios showed that there is no one example of specific use of menthol and camphor in combination as eutectic mixture in order to improve solubility of an included drug. All anti-inflammatory components used in such formulations are liquid (methylsalycilate, benzylnicotinate, etc.) and easily miscible with oil components of the creams or ointments. There is no limitation for solubility, and these topicals can contain up to 60% of active component, e.g., methylsalycilate), Altadonna (U.S. Pat. No. 5,853,768).

In the documentation there has not been a recognition of a menthol-to-camphor ratio in the eutectic region. In all cases, the existing preperations are used only due to their mild irritative or anti-inflammatory activity (camphor, nicotinic acid derivatives) or skin penetration enhancement properties of menthol itself.

It has now been recognized that a radical increase of drug solubility in a eutectic mixture of polar hydrophobic compounds allows preparation of effective and safe topical formulations with these drugs for external application.

Having thus described the invention, reference will now be made to the accompanying drawings illustrating preferred embodiments.

BRIEF DESCRIPTION OF THE DRAWINGS

Similar numerals in the figures denote similar elements.

DETAILED DESCRIPTION OF THE PREFERRED EMBODIMENTS

A mixture of equimolar amounts of crystalline camphor and menthol at room temperature immediately led to liquified crystals. This mixture was used in the preparations as an effective solvent for some NSAID compounds.

Figure 1:
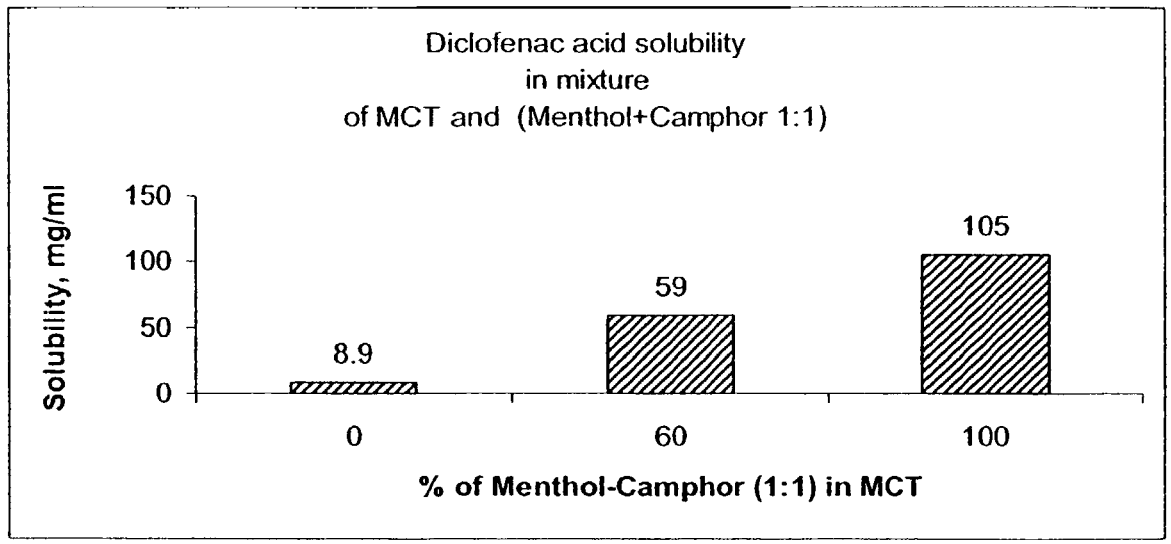
FIG. 1 is a graphical representation of anti-inflammatory solubility in a mixture of MCT and a menthol/camphor mixture.

FIG. 1 graphically represents the solubility of Diclofenac (as free acid) in mixtures of medium chain triglycerides (MCT, standard oil vehicle, Labrafac® TGCC) with different levels of added menthol-camphor eutectic mixture. Diclofenac saturation concentration at 25° C. was evaluated by HPLC. Solubility in a pure equimolar menthol-camphor eutectic mixture was found to be 11.8 times higher than in pure MCT.

Figure 2:
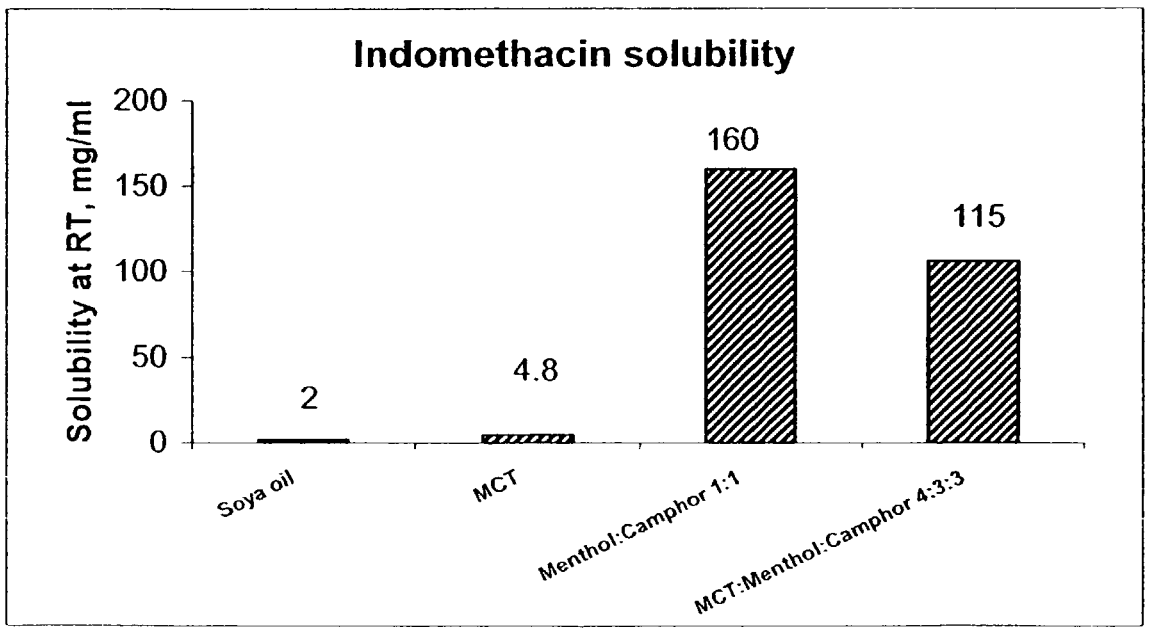
FIG. 2 is a graphical representation of Indomethacin solubility in oleaginous vehicles and in a menthol/camphor vehicle.

Similar behavior was observed also for Indomethacin, illustrated graphically in FIG. 2, maximum solubility in equimolar eutectic menthol-camphor mixture is 160 mg/ml, compared with 2 mg/ml in the soy oil or 4.8 mg/ml in MCT oil. For comparison, Ho et. al. "Penetration Enhancement by Menthol Combined with a Solubilization Effect in a Mixed Solvent System", J. Controlled Release 1998, February 12; 51(2–3), pp. 301–11, investigated influence of menthol addition (up to 12% by weight) as solubility enhancer for Indomethacin in different pharmaceutical vehicles such as water, ethanol, propylene glycol and their combinations. In any case the maximum solubility hardly reached 2% (approximately 20 mg/ml).

Figure 3:
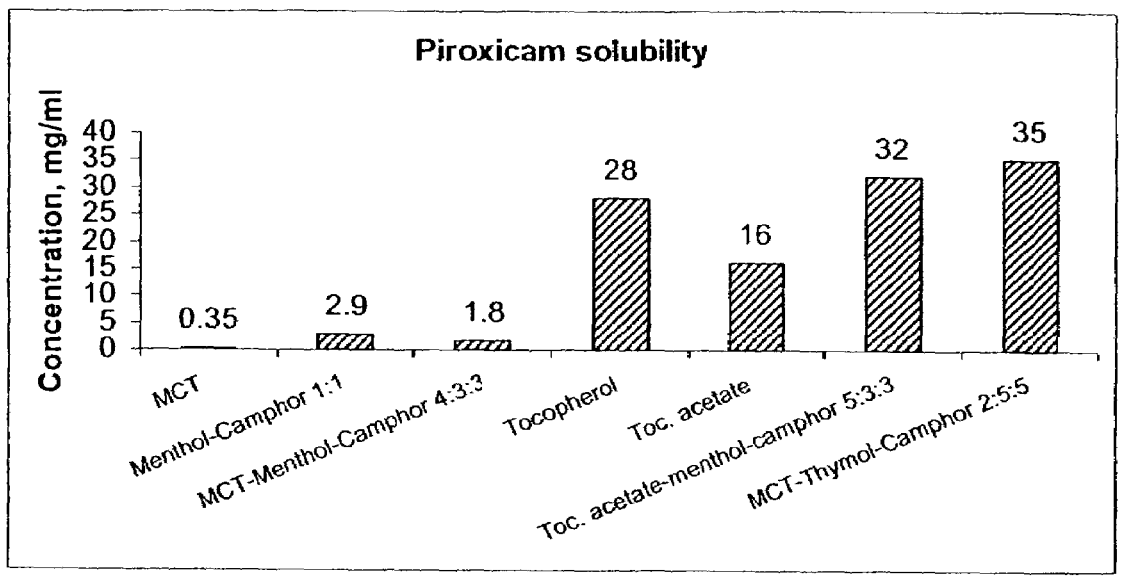
FIG. 3 is a graphical representation of Piroxicam solubility in oleaginous vehicles and in a eutectic vehicle.

In FIG. 3, further graphic data are presented for Piroxicam.

Piroxicam solubility is significantly lower than aromatic NSAIDs, however, use of the eutectic menthol-camphor mixture increased drug solubility at room temperature between 8 and 11 times, from 0.35 mg/ml in MCT to 2.9–3.2 mg/ml in pure eutectic mixture and to 1.8 mg/ml in MCT with 60% menthol-camphor (1:1) content.

If alpha-tocopherol or tocopherol acetate is used as the oil phase, solubility can reach 30–35 mg/ml for tocopherol-menthol-camphor composition 5:3:3 (parts by weight).

Use of other ratios for menthol-camphor eutectic mixture (e.g., 2:1 or 1:2; 3:4 or 4:3) also improves solubility for most of investigated substances but in slightly lower extent. Very significant improvement in solubility was achieved with replacement of menthol for another eutectic forming substance, thymol (2-isopropyl-5-methylphenol, thyme oil component).

Obtained solutions of NSAIDs in lipid phase containing menthol-camphor or another eutectic mixture vehicle are stable in wide temperature range and non-irritating for human and animal skin (Dreize' test). Based on these observations different topical formulations with NSAIDs were prepared and will now be discussed in the examples.

EXAMPLE 1

Indomethacin 1% Cream

| CREAM INGREDIENTS | % | Per 250 g cream |
|---|---|---|
| Indomethacin USP | 1.00 | 2.5 |
| Medium Chain Triglycerides (Labrafac ® CCTG) | 4.00 | 10 |
| Soy Lecithin (Phospholipon ® S-80) | 1.00 | 2.5 |
| (±) Camphor USP | 3.00 | 7.5 |
| L-(−)-Menthol USP | 3.00 | 7.5 |
| Tween ™-80 (Polysorbate 80, USP) | 1.60 | 4.0 |
| TPGS (Tocopherol polyethylene glycol 1000 succinate) | 0.80 | 2.0 |
| Sodium Ethylenediamine tetraacetate (EDTA sodium) | 0.10 | 0.25 |
| Carbopol ® 971P | 1.50 | 3.75 |

-continued

| CREAM INGREDIENTS | % | Per 250 g cream |
|---|---|---|
| Glycerin USP | 2.50 | 6.25 |
| Water | 81.50 | 203.75 |

Vehicle (eutectic mixture) preparation:
(±) Camphor and L-Menthol were mixed together during heating at between 40 and 50° C. until a clear liquid was obtained.

Oil Phase Preparation:

Soy lecithin, MCT oil and TPGS were mixed together at 45° C. until a homogenous solution was obtained. Tween™-80 as then added, followed by the addition of the eutectic mixture vehicle. The mixture was stirred until completely dissolved. Indomethacin (USP grade) was added to the warm mixture and stirred for 10 minutes at 45° C. until completely dissolved.

Water Phase Preparation:

EDTA disodium salt, glycerin and Tween™-80 were added to water (90% of calculated amount) and stirred until completely dissolved.

Emulsification:

The solution was combined with the oil phase, mixed thoroughly using appropriate mixer and homogenized using high pressure homogenizer (Avestin® C-5) at 8,000–12,000 psi, (600–800 bar). The mixture was passed through the homogenizer between 2 and 3 times.

Cream Preparation:

In a separate vessel Carbopol® 971 P was mixed with 10% of calculated amount of water and soaked for between 2 and 6 hours. Carbopol® paste was combined with the homogenized emulsion using a high shear rotor-stator type mixer (Omni GLH mixer) at 18,000–24,000 rpm. Triethanolamine was added gradually while mixing until the desired pH and viscosity were achieved.

EXAMPLE 2

Indomethacin 2% Cream

The composition was prepared in accordance with the methodology of Example 1.

| CREAM INGREDIENTS | Per 100 g cream | Per 1000 g |
|---|---|---|
| Lipid Phase | | |
| Indomethacin USP | 2.00 | 20.00 |
| Medium Chain Triglycerides (Labrafac ® CCTG) | 8.00 | 80.00 |
| Egg Lecithin S-75 | 2.00 | 20.00 |
| (±) Camphor USP | 6.00 | 60.00 |
| L-(−)-Menthol USP | 6.00 | 60.00 |
| Tween ™-80 (Polysorbate-80 USP) | 2.00 | 20.00 |
| TPGS (Tocopherol polyethylene glycol 1000 succinate) | 0.80 | 8.00 |
| Water Phase | | |
| Sodium Ethylenediamine tetraacetate (EDTA sodium) | 0.10 | 1.00 |
| Bronopol ® (2-Brom-2-nitro-1,3-propanediol) | 0.10 | 1.00 |
| Triethanolamine | 0.50 | 5.00 |
| Ultrez ™ 10 | 0.50 | 5.00 |
| Glycerin | 2.20 | 22.00 |
| Water | 69.80 | 698.00 |

Bronopol® (2-Brom-2-nitro-1,3-propanediol) was added to the water phase as an antibacterial preservative. Ultrez™ was used as a viscosity regulating component instead of Carbopol® without the preliminary hydration step as set forth in Example 1.

EXAMPLE 3

Diclofenac Sodium 1% Cream

The composition of the emulsion for 1% Diclofenac cream presented in Table 3. The cream contains approximately 14% of the oil phase with a ratio MCT: Camphor: Menthol of 6:3:4.

| CREAM INGREDIENTS | Per 100 g cream |
|---|---|
| Medium Chain Triglycerides (Labrafac ® CCTG) | 6.00 |
| (±) Camphor USP | 3.00 |
| L-(−)-Menthol USP | 4.00 |
| Tocopherol succinate | 0.02 |
| Soy Lecithin (Phospholipon ® S-80) | 0.12 |
| Tween ™-80 (Polysorbate-80) | 2.00 |
| Diclofenac Sodium USP | 1.00 |
| Water | 80.38 |
| Hydrochloric acid 1N | 3.5 |

The oil phase was prepared by dissolving MCT, oil Tocopherol succinate, lecithin, camphor, and menthol at 45° C.

The water phase was prepared by dissolving Diclofenac sodium and Tween™-80 in hot 85° C. purified water.

After mixing the warm oil and hot water phases, hydrochloric acid was added to coarse emulsion while intensive stirring. The pH was adjusted to between 3.5 and 4.2. Homogenization was conducted as described in Example 2. After a fine emulsion was obtained, it was filtered through 0.45 micron PTFE membrane filter. The emulsion was used for cream preparation by addition of Carbopol® 971 as a gelling agent to a final concentration of 1.5% with pH adjustment to between 4.5 and 5.0.

1.5% Diclofenac sodium emulsion (high loading) was prepared by a similar manner. The composition is identical to that tabulated in Table 3. Balance was adjusted with water and hydrochloric acid.

EXAMPLE 4

Ibuprofen 5% Cream

5% Ibuprofen cream was prepared as described in Example 2. The composition of the emulsion for 5% Diclofenac cream is presented in Table 4. The cream contains approximately 26% of the oil phase with a ratio MCT: Camphor: Menthol of approximately 4.25:1:1.

| CREAM INGREDIENTS | Per 100 g cream | Per 300 g |
|---|---|---|
| Ibuprofen | 5.00 | 15.00 |
| Medium Chain Triglycerides (Labrafac ® CCTG) | 13.75 | 41.25 |
| Soy Lecithin (Phospholipon ® S-80) | 1.20 | 3.60 |
| (±) Camphor USP | 3.25 | 9.75 |
| L-(−)-Menthol USP | 3.25 | 9.75 |
| Tween ™-80 (Polysorbate-80, USP) | 2.00 | 6.00 |

-continued

| CREAM INGREDIENTS | Per 100 g cream | Per 300 g |
|---|---|---|
| TPGS (Tocopherol polyethylene glycol 1000 succinate) | 0.80 | 2.40 |
| Sodium Ethylenediamine tetraacetate (EDTA sodium) | 0.10 | 0.30 |
| Bronopol ™ | 0.10 | 0.30 |
| Triethanolamine | 1.00 | 3.00 |
| Carbopol ® 934P | 1.00 | 3.00 |
| Glycerin | 2.20 | 6.60 |
| Water | 66.35 | 398.10 |

EXAMPLE 5

Piroxicam 0.5% Cream

The composition was prepared by the method described in Example 4, but L-(−)-menthol was replaced with thymol (2-isopropyl-5-methylphenol). The cream contained approximately 28% of the oil phase with a ratio MCT: Camphor: Thymol:Tocopherol acetate of approximately 2:5:5:2.

| CREAM INGREDIENTS | Per 100 g cream | Per 250 g |
|---|---|---|
| Piroxicam | 2.00 | 5.00 |
| Medium Chain Triglycerides (Labrafac ® CCTG) | 3.00 | 7.50 |
| Soy Lecithin (Phospholipon ® S-80) | 2.00 | 5.00 |
| (±) Camphor USP | 7.50 | 18.75 |
| Thymol | 7.50 | 18.75 |
| Tween ™-80 (Polysorbate-80, USP) | 2.50 | 6.25 |
| Tocopherol acetate (Vitamine E acetate) | 2.00 | 5.00 |
| EDTA | 0.10 | 0.25 |
| Carbopol ® 934P | 1.50 | 3.75 |
| Glycerin | 2.20 | 5.50 |
| Triethanolamine | 0.90 | 2.25 |
| Water | 69.70 | 174.25 |

EXAMPLE 6

Reference

Emulsion with Indomethacin, prepared according to U.S. Pat. No. 6,113,921.

| | Per 100 g cream | |
|---|---|---|
| CREAM INGREDIENTS | 0.5% Indo (low loading) | 1.0% Indo (high loading) |
| Indomethacin | 0.5 | 1.0 |
| Medium Chain Triglycerides (MCT oil) | 17.0 | 17.0 |
| Egg Lecithin (Phospholipon ® E-80) | 0.8 | 0.8 |
| Emulphor EL-620 (polyethoxylated castor oil) | 1.6 | 1.6 |
| Carbopol ® 940 | 1.7 | 1.7 |
| Glycerin | 2.2 | 2.2 |
| EDTA sodium salt | 0.05 | 0.05 |
| Tocopherol acid succinate | 0.04 | 0.05 |
| Triethanolamine | 0.65 | 0.65 |
| Water | 75.3 | 74.5 |

Indomethacin (0.5 g for low loading and 1.0 g for high loading emulsions) was dissolved in a preheated (60° C.) mixture of egg lecithin, tocopherol succinate and MCT oil.

This mixture was emulsified with a water phase (water with Emulfor EL-620, EDTA sodium and glycerin) using a high shear mixer for 5 minutes at 20,000 rpm to form an emulsion.

Further treatment of the emulsion was conducted in a high pressure homogenizer at 800 bar (12,000 psi) for 6 cycles. Thereafter, the emulsion was cooled to room temperature, and pH was adjusted to between 5.6 and 6.5. Part of emulsion was gelled using Carbopol® 940 to form a cream; another part was stored at room temperature in tightly closed amber glass containers for 6 months to observe the physical stability.

Diclofenac sodium (1.0% and 1.5% drug loading) emulsions were prepared in a similar manner to Example 6.

Figure 4:
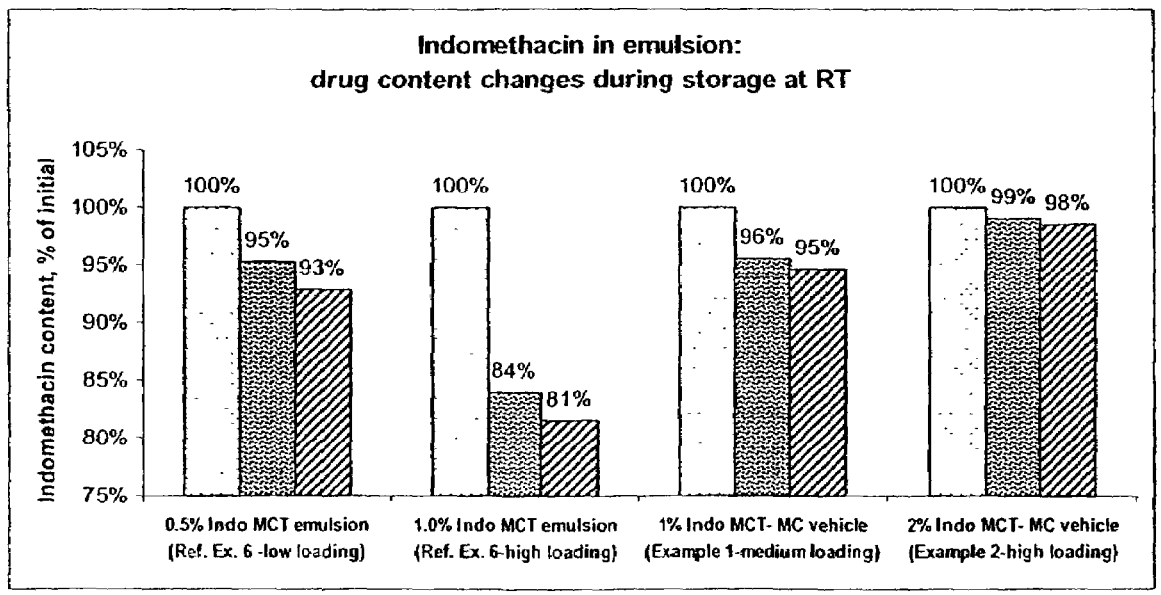
FIG. 4 is a graphical representation of drug content change during storage.

To estimate drug precipitation, the stored emulsion samples either for the reference Example 6, low and high loaded or invention related (Examples 1 and 2) were filtered through PTFE membrane filters. The Indomethacin content in the filtrates was measured using the HPLC method. FIG. 4 illustrates the results.

Low loaded emulsion, prepared in accordance with U.S. Pat. No. 6,113,921, showed reasonable stability during storage, but with an increase in the initial Indomethacin loading, the final concentration of non-precipitated drug decreases drastically. In contrast, the eutectic mixture vehicle emulsion, prepared in accordance with the present invention, maintains drug content.

Similar results have been obtained for Diclofenac sodium emulsions. In a composition containing 1% of the drug, stability for both formulations was observed. In a composition containing 1.5% Diclofenac sodium emulsion in the menthol-camphor eutectic mixture, stability was observed for at least 3 months at room temperature, while identically loaded reference emulsion demonstrated significant drug precipitation during the same period.

Anti Inflammatory Activity "In Vivo":

Investigations on animals (rats, carrageenan induced paw edema model) showed significant anti-inflammatory action of the topically applied compositions containing the eutectic vehicle.

AUC ratio for edema volume (calculated by trapezoidal rule for t=0–6 hours).

| Control (non-treated) | Indomethacin cream (example 2)-2 mg of Indomethacin/rat | Indomethacin gel (Sumitomo Pharm.) 2 mg of Indomethacin/rat |
|---|---|---|
| 100% | 32% (±12%) | 114% (±39%) |

Although embodiments of the invention have been described above, it is not limited thereto and it will be apparent to those skilled in the art that numerous modifications form part of the present invention insofar as they do not depart from the spirit, nature and scope of the claimed and described invention.

We claim:

1. A composition for topical application comprising a non-steroidal anti-inflammatory drug selected from the group consisting of diclofenac and piroxicam and a solvent vehicle for solubilizing said non-steroidal anti-inflammatory drug, said solvent vehicle consisting essentially of: a liquid eutectic mixture of camphor and menthol and optionally a liquid hydrophobic component, wherein the camphor and menthol are present in the eutectic mixture in a ratio from 4:1 to 1:4.

2. The composition of claim 1, wherein the ratio of said camphor and menthol are present in said eutectic mixture in a ratio from 2:1 and 1:2.

3. The composition of claim 1 wherein the drug is diclofenac.

4. The composition of claim 1 wherein the drug is piroxicam.

5. The composition of claim 1 wherein said camphor is selected from the group consisting of D-isomer, L-isomer, racemic camphor or a mixture of camphor isomers.

6. The composition of claim 1 wherein said menthol is selected from the group consisting o D-isomer, L-isomer, racemic menthol or a mixture of menthol isomers.

7. The composition of claim 1 wherein the hydrophobic component is tocopherol.

8. The composition of claim 7, wherein the tocopherol is alpha-tocopherol or tocopherol acetate.

9. A composition for topical application comprising a non-steroidal anti-inflammatory drug selected from the group consisting of: diclofenac, piroxicam, and indomethacin, and a solvent vehicle for solubilizing said non-steroidal anti-inflammatory drug, said solvent vehicle consisting essentially of: medium chain triglycerides and a liquid eutectic mixture of camphor and menthol and optionally a liquid hydrophobic component, wherein the camphor and menthol are present in the eutectic mixture in a ratio from 4:1 to 1:4.

10. The composition of claim 9, wherein the ratio of said camphor and menthol are present in said eutectic mixture in a ratio from 2:1 to 1:2.

11. The composition of claim 9 wherein the drug is diclofenac.

12. The composition of claim 9 wherein the drug is piroxicam.

13. The composition of claim 9 wherein the drug is indomethacin.

14. The composition of claim 9 wherein said camphor is selected from the group consisting of D-isomer, L-isomer, racemic camphor or a mixture of camphor isomers.

15. The composition of claim 9 wherein said menthol is selected from the group consisting of D-isomer, L-isomer, racemic menthol or a mixture of menthol isomers.

16. The composition of claim 9 wherein said hydrophobic component is tocopherol.

17. The composition of claim 16, wherein the tocopherol is alpha-tocopherol or tocopherol acetate.

18. A composition for topical application comprising the non-steroidal anti-inflammatory drug piroxicam and a solvent vehicle for solubilizing piroxicam, said vehicle consisting essentially of: medium chain triglycerides and a liquid eutectic mixture of camphor and thymol and optionally a liquid hydrophobic component, wherein the MCT:camphor:thymol are present in a ratio of 2:5:5.

19. The composition of claim 18 wherein said camphor is selected from the group consisting of D-isomer, L-isomer, racemic camphor or a mixture of camphor isomers.

20. The composition of claim 18 wherein the hydrophobic component is tocopherol.

21. The composition of claim 20, wherein the tocopherol is alpha-tocopherol or tocopherol acetate.

* * * * *